(12) United States Patent
Van Den Houten et al.

(10) Patent No.: US 8,774,363 B2
(45) Date of Patent: Jul. 8, 2014

(54) MEDICAL VIEWING SYSTEM FOR DISPLAYING A REGION OF INTEREST ON MEDICAL IMAGES

(75) Inventors: Peter Van Den Houten, Eindhoven (NL); Nicolaas Hylke Bakker, Eindhoven (NL); Raoul Florent, Ville Davray (FR); Vincent Maurice Andre Auvray, Paris (FR)

(73) Assignee: Koninklijke Philips N.V., Eindhoven (NL)

( * ) Notice: Subject to any disclaimer, the term of this patent is extended or adjusted under 35 U.S.C. 154(b) by 349 days.

(21) Appl. No.: 13/203,266

(22) PCT Filed: Mar. 1, 2010

(86) PCT No.: PCT/IB2010/050873
§ 371 (c)(1),
(2), (4) Date: Aug. 25, 2011

(87) PCT Pub. No.: WO2010/100596
PCT Pub. Date: Sep. 10, 2010

(65) Prior Publication Data
US 2011/0305322 A1    Dec. 15, 2011

(30) Foreign Application Priority Data

Mar. 6, 2009 (EP) .................................. 09305208

(51) Int. Cl.
*H05G 1/64* (2006.01)

(52) U.S. Cl.
USPC ...................................................... 378/98.12

(58) Field of Classification Search
USPC .................. 378/62, 91, 98, 98.2, 98.5, 98.12
See application file for complete search history.

(56) References Cited

U.S. PATENT DOCUMENTS

| 5,345,938 | A | 9/1994 | Nishiki |
| 5,896,463 | A | 4/1999 | Kuhn |
| 2006/0058643 | A1 | 3/2006 | Florent et al. |
| 2008/0009715 | A1 | 1/2008 | Kukuk et al. |
| 2008/0027316 | A1 | 1/2008 | Baumgart |
| 2008/0045827 | A1 | 2/2008 | Rongen et al. |

FOREIGN PATENT DOCUMENTS

| WO | WO0036826 | 6/2000 |
| WO | WO03045263 | 6/2003 |
| WO | WO03049032 | 6/2003 |

*Primary Examiner* — Jurie Yun

(57) ABSTRACT

A medical viewing system with an X-ray image acquisition device for acquiring angiograms and interventional live images of vessels is adapted for generating a region of interest border into which an object referenced by an object-based registration process must extend in order to achieve an accurate registration of vessel trees extracted from the angiogram and the live images. The region of interest border is then overlaid onto the vessel tree images and the live images. The medical viewing system reminds the person accomplishing the intervention of the importance of pushing the object far enough into the image, while being discrete enough to be ignored if preferred, thus yielding in a reliable and precise road mapping processing.

20 Claims, 4 Drawing Sheets

MEDICAL VIEWING SYSTEM FOR DISPLAYING A REGION OF INTEREST ON MEDICAL IMAGES

FIELD OF THE INVENTION

The present invention is related to a medical viewing system and a method for displaying a region of interest on medical images representing positioning devices in a blood vessel.

BACKGROUND OF THE INVENTION

For the purpose of interventions, for example as applied in catheter labs under fluoroscopy when treating coronary stenoses, it is known to visualize vessel structures and devices advanced inside the vessel structures. Hereby, firstly a contrast agent is injected via a catheter and an X-ray examination apparatus records an angiographic sequence, which is also called an "angiogram", that shows the vessels that are radio-opaque when filled with the contrast agent. Secondly, during the intervention, for example a flexible, partially or fully radio-opaque guide wire is advanced to affected vascular structures and by means of low-dose fluoroscopic X-ray surveillance the guide wire is visualized, which is referred to as "live images". By means of an overlay technique the angiogram and live images are overlaid so that a medical image containing the vessel structures and the device at the same time can be created. This technique is referred to as "road mapping" that allows for the hand-eye coordination while advancing the device, e.g. a guide wire.

For the navigation of devices within the vessels a subjective visual fusion of the static angiogram and the live fluoroscopy images is required. Since the angiogram contains a number of distinct images that are shifted relative to each other and are acquired at different times, e.g. over one complete cardiac cycle and the vessels in the live images are moving, an accurate method for this road mapping is mandatory.

A way to achieve the road mapping procedure is to choose an object-based process, wherein firstly arteries are extracted from the angiogram, yielding a cardiac cycle of artery tree images. A targeted object in the live images is chosen as a spatial reference. Secondly, the artery tree images are shifted and superimposed to the live fluoroscopic images according to the targeted object in order to better cover the live interventional devices.

SUMMARY OF THE INVENTION

The success and the accuracy of this road mapping technique greatly lies on the presence of the targeted objects in the live image. As a targeted object, for example a catheter tip may be chosen which is utilized during interventional procedures, typically for a percutaneous coronary intervention ("PCI"). However, if the expected object, e.g. the catheter tip, is only partially visible in the acquired live images, the results of a related object-based registration algorithm is ill-posed and may lead to no solution or to a multitude of solutions, among which every one but one are erroneous.

It is difficult to make the clinician aware of the importance of the visibility of key objects for the success of the road mapping procedure. Instead, the clinician occupied with the intervention, naturally focuses primarily on the intervention. Further, it is difficult to assess how much the considered object should be in the image when one is not familiar with the details of the related road mapping processing. Even if one specifies precisely the conditions to be fulfilled for the processing success and the required accuracy, e.g. a certain visible length of the object in millimeters, or a certain number of pixels, at intervention time, fulfilling those precise specifications is a burden for the clinician.

Accordingly, there may be a need for a medical viewing system which may allow to overcome at least some of the above insufficiencies. Particularly, there may be a need for a medical viewing system that provides an accurate road mapping in ensuring the sufficient visibility of reference objects for detection of real cardiac phases of live fluoroscopy images.

These needs may be reached with a medical viewing system, a method, a computer program element and a computer readable medium according to the independent claims. Various embodiments of the present invention are described in the dependent claims.

The medical viewing system according to the present invention may provide the following method.

First, a pre-interventional static diagnostic angiogram of vessels with injected contrast agent is acquired with at least one X-ray image acquisition device. Secondly, during intervention live fluoroscopic image acquisition of the interventional area by means of the X-ray image acquisition device in order to visualize interventional devices is accomplished. The necessary visual fusion of the static angiogram and the live images is realized by a road mapping technique, by which the static angiogram is registered relative to the live images in order to geometrically fit them. This road mapping may be provided by an object-based process, whereby the success and the accuracy greatly lies on the presence of targeted objects in the live images. In the following an interventional device, e.g. a catheter and preferably a tip of the catheter, may be chosen as a targeted object. It is pointed out that all sorts of distinctive objects may be chosen as targeted object for the object-based registration, e.g. a pacemaker lead, electrodes, needles etc. The invention is not limited to the use of catheter tips as targeted objects.

A calculation unit, which is connected to the X-ray image acquisition device and at least one display unit, is adapted for generating a region of interest border into which the considered targeted object must extend in order to achieve a pre-determined accuracy of the object-based image registration. The generated border is then overlaid onto the registered images containing the live fluoroscopy images and the vessel tree visualization as an indication for a clinician.

It is to be noted that the above-described method provides an optical assistance during for example interventional procedures, like percutaneous coronary intervention as applied in catheter labs when treating coronary stenoses. The assistance may be used similarly for other applications.

A gist of the present invention is to display the limit of a region in which the considered targeted object must be partially present to ensure an optimal processing of the road mapping procedure. A clinician positioning the targeted object within this region will have brought it far enough in the image. The medical viewing system according to the present invention reminds the clinician of the importance of pushing the object far enough into the image, while being discrete enough to be ignored if preferred. The clinician expecting a reliable road mapping must provide enough information to allow its computation. By displaying a region of interest over the image the invention invites him to push e.g. a catheter injection tip far enough into the image to constrain the superimposition problem enough. This leads to a more reliable and precise road mapping processing.

According to an exemplary embodiment of the present invention, the region of interest border is positionable relative to a shutter position. The shutter is preferably positioned between the table and the patient and limits X-ray exposition to the interventional area on the patient. Since the considered targeted object must be visible in the acquired X-ray images it is necessary to respond to the shutter position, because the considered object may not be visible due to a misplaced or a too narrow shutter. It is desirable to always define a stripe or a gap between the image borders and the region of interest borders for the targeted object to have the minimum necessary amount of pixels or the right size in the image. Here, the expression "image borders" refer to the actual outer edges of the acquired X-ray image that depend on the X-ray exposed area inside the opening of the shutter.

According to another exemplary embodiment, the calculation unit is adapted for generating region of interest borders with edges that are arranged in a parallel manner to the edges of the shutter. Thus, the gap between the edges of the image border and the related edges of the region of interest border do not vary, so that the accuracy of the object-based registration can be maintained within each area of the x-ray image.

In a further exemplary embodiment of the present invention the size of the region of interest border is adaptable to various geometry parameters, for example the zoom factor, the shutter geometry, angulation or rotation angle of the X-ray image acquisition device etc. Therefore, it is not mandatory to exclusively generate a rectangular region of interest border, other border shapes may also be desired, depending on the intervention. The calculation unit preferably reacts to various geometry parameters in order to maintain the predetermined accuracy for the object-based registration. On changing the angulation or rotation of the X-ray image acquisition device the considered targeted object may be disappear or become hardly visible in the acquired image and thus, the accuracy of the object-based registration decreases. Therefore, the region of interest border should be adapted to this situation in order to direct the clinician to move the object further into the region of interest. It is also preferable that the calculation unit is adapted for considering the geometry parameters in real time so that it may change the shape and the size of the region of interest border any time when a geometry parameter changes.

The size of the region of interest border generated by the calculating unit is adaptable to anatomical priors in a further embodiment of the present invention. This enables the medical viewing system according to the present invention to adapt to different tasks and different interventional areas of the patient. During percutaneous coronary intervention a larger region of interest border may be needed than in other interventional procedures where the related organs do not move as heavily as in the heart region.

In a further exemplary embodiment of the present invention the system provides the ability for an exam phase determination in order to adapt the region of interest border overlay on the display unit and to remove the overlaid border respectively. For example, during fluoroscopy live image acquisition all advantages of the present invention can be taken. On the other hand, during acquisition of the angiograms it is not necessary and may also be distracting to see the region of interest border.

According to a still further embodiment of the present invention the overlay of the border of the region of interest on the display unit can be switched off manually, leading to less distraction of the clinician if it is considered clear—preferably by the medical viewing system according to the present invention—that the considered targeted object for the object-based registration is situated inside the related region of interest.

Further exemplary embodiments of the medical viewing system are set forth in the dependent claims. The expected advantages discussed in relation to the exemplary embodiments of the medical viewing system described above also apply to the exemplary embodiments of the method according to the invention and vice versa.

According to another exemplary embodiment of the present invention, a computer readable medium is provided in which a computer program for generating and overlaying a region of interest border onto vessel tree images and live images is stored which, when being executed by a processor, causes the processor to carry out the above mentioned steps.

Furthermore, according to another exemplary embodiment of the present invention, a computer program element for generating and overlaying a region of interest border onto vessel tree images and live images is provided which, when being executed by a processor, causes the processor to carry out the above mentioned steps.

Those skilled in the art will readily appreciate that the method of generating an overlay of a region of interest border onto vessel tree images and live images according to the invention may be embodied as a computer program, i.e. by software or may be embodied using one or more special electronic optimization circuits, i.e. in hardware, or the method may be embodied in hybrid form, i.e. by means of software components and hardware components.

This exemplary embodiment of the invention covers both a computer program that right from the beginning uses the invention and a computer program that by means of update turns an existing program into a program that uses the invention.

Further on, the computer program element may be able to provide all necessary steps to fulfill the procedure of the method as described above.

According to a further exemplary embodiment of the present invention, a medium for making a computer program element available for downloading is provided, which computer program element is arranged to perform the method, according to one of the previously described embodiments of the invention.

For example, existing medical viewing systems may be upgraded with a new software, which, when being executed on a processor, causes the system to carry out the above-mentioned steps in overlaying a region of interest border onto vessel tree images and live images according to the invention.

It has to be noted that features and side effects of the present invention have been described with reference to different embodiments of the invention. However, a person skilled in the art will gather from the above and the following description that unless other notified, in addition to any combination or features belonging to one embodiment also any combinations between features relating to different embodiments or to a manufacturing method is considered to be disclosed with this application.

BRIEF DESCRIPTION OF THE DRAWINGS

Features and desired effects of the present invention will be further described with respect to specific embodiments as shown in the accompanying figures but to which the invention shall not be limited. The drawings in the figures are only schematically and not to scale. Similar elements in the figures are referred to with similar reference signs.

DETAILED DESCRIPTION OF EMBODIMENTS

Figure 1:
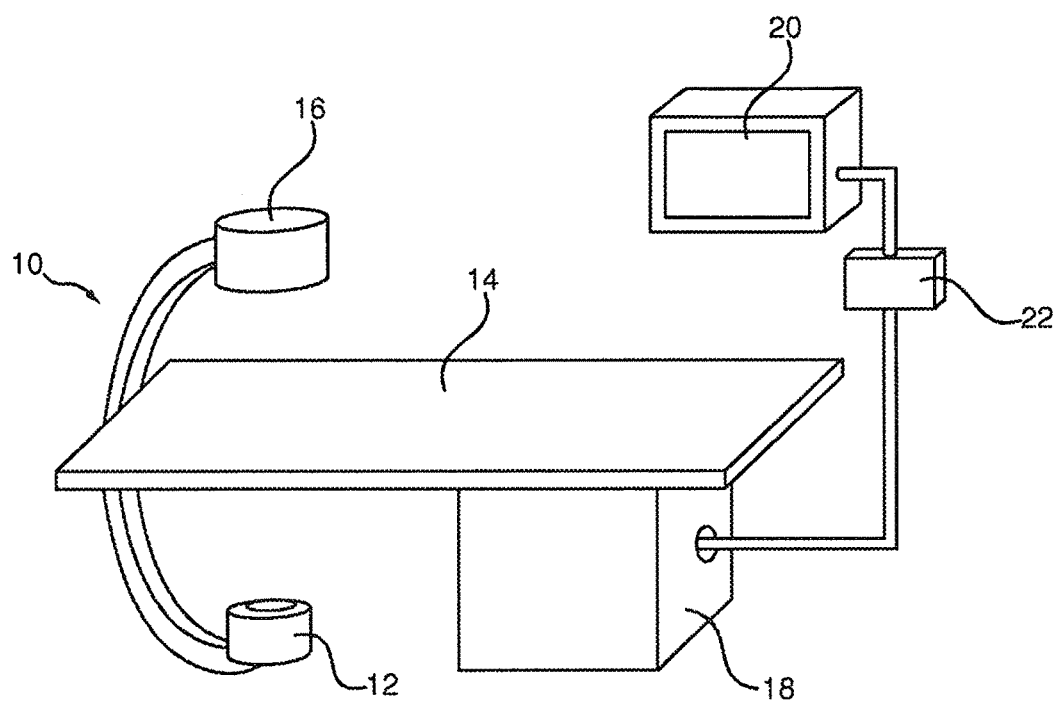
FIG. 1 shows an X-ray imaging system with an integrated medical viewing system according to the invention.

FIG. 1 schematically shows an X-ray imaging system 10 with a medical viewing system for generating a region of interest border and overlaying the border on vessel tree images and live images.

The X-ray imaging system 10 comprises an X-ray image acquisition device with a source of X-ray radiation 12 provided to generate X-ray radiation. A table 14 is provided to receive a subject to be examined. Further an X-ray image detection module 16 is located opposite the source of X-ray radiation 12. During the radiation procedure the examined subject is located between the source of X-ray radiation 12 and the detection module 16. The latter sends data to a data processing unit or calculation unit 18, which is connected to both the X-ray image detection module 16 and the X-ray radiation source 12. The calculation unit 18 is exemplarily located underneath the table 14 for saving space within the examination room. Of course, it could also be located at a different place, such as in a different room or a different laboratory. Furthermore, a display unit 20 is arranged in the vicinity of the table 14 for displaying information to the person operating the X-ray imaging system, which can be a clinician such as a cardiologist or cardiac surgeon. Preferably, the display unit 20 is movably mounted to allow for an individual adjustment depending on the examination situation. Also, an interface unit 22 is arranged to input information by the user.

Basically, the image detection module 16 generates images by exposing the subject to X-ray radiation, wherein said images are further processed in the calculation unit 18. It is noted that the example shown is of a so called C-type X-ray image acquisition device. The X-ray image acquisition device comprises an arm in form of a C where the image detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

Figure 2:
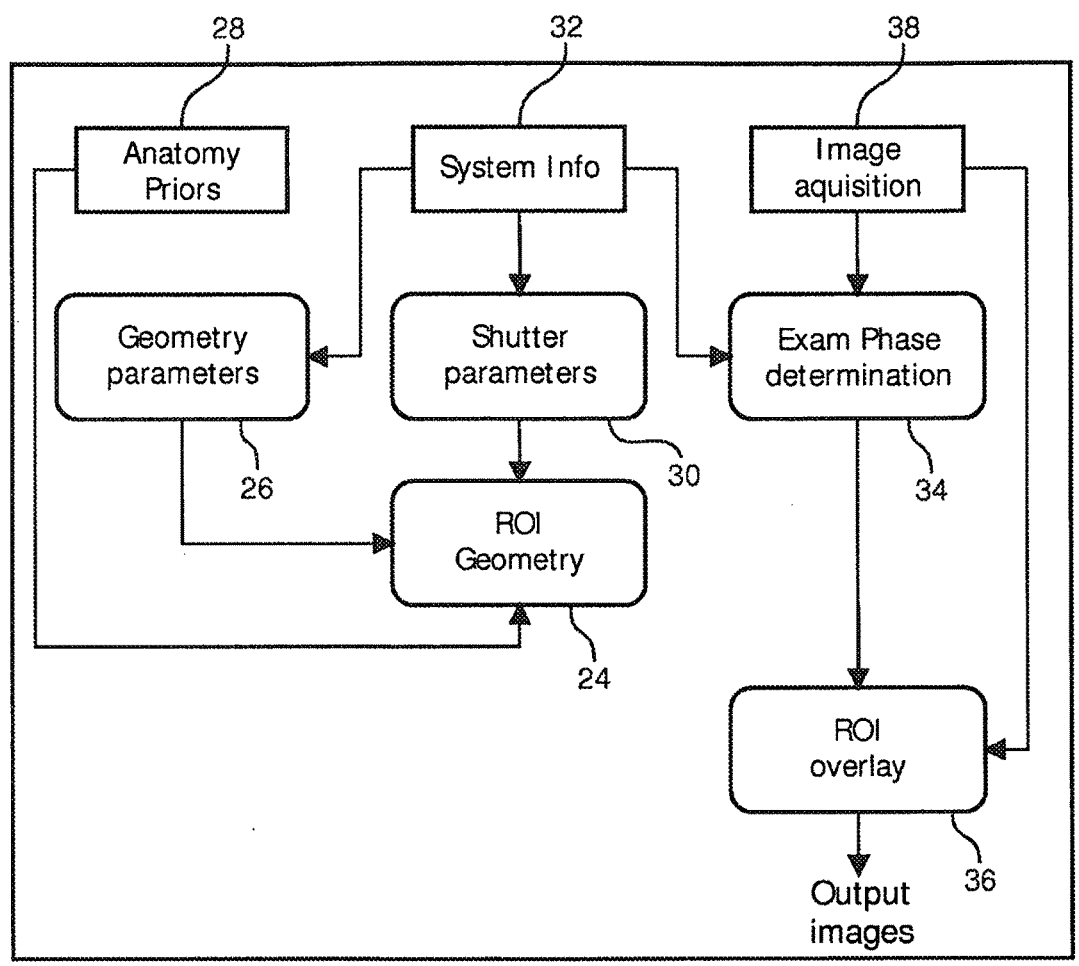
FIG. 2 schematically describes the steps for generating and overlaying a region of interest border on vessel tree images and live images according to the invention.

FIG. 2 schematically shows method steps provided by a medical viewing system according to the present invention. Generating a region of interest border geometry 24 by means of the calculation unit 18 can be seen as the core element in this diagram. For being able to conduct the generate the borders a number of input parameters are necessary, e.g. geometry parameters 26 including several geometrical parameters, for example zoom of the acquired image, the angulation and rotation angles of the C-arm 10 and other geometrical parameters are provided.

Additionally, anatomy priors 28 are further provided as input parameters for ideally taking anatomical and prior interventions into account.

Also, shutter parameters 30 containing the shutter position, the shutter size and the shutter shape is provided as still further input parameters for the geometry generation. The shutter blocks X-rays before reaching the patient to be examined in order to limit the X-ray exposed area of the patient. Since outside of shutter borders no X-ray detection is possible, the presence of the considered targeted object in the live images may be blocked by the shutter and thus, the shutter position, the shape and the size must be taken into consideration.

The shutter parameters 30 and the geometry parameters 26 may be provided through system information 32, wherein the calculation unit 18 or any other device provides all relevant measured or stored information about the related X-ray image acquisition device and of the medical viewing system.

The geometry generation may include the generation of a box—which is not necessarily a rectangular box but can comprise any suitable shape—with edges parallel to the edges of the shutter and set to leave a gap corresponding to a fixed ratio of the image. The dimensions of the gap may be set experimentally by the developers of the object-based registration algorithm to ensure that the considered targeted object within the central region of interest is defined enough for optimal processing. In the case of road mapping procedures, the gap may be worth 10 to 20% of the image dimension. The invention is not limited to such a fraction of the image dimensions. Depending on the intervention purpose it the fraction can as well be smaller or larger.

Further to the generation of the region of interest geometry, the system according to the present invention desirably determines the present exam phase 34 in order to activate or deactivate the overlaying of the region of interest border or to regulate its boldness yielding in a system according to the present invention to be not over intrusive and appearing and disappearing depending on the intervention phase. The determination might be provided automatically so that, for instance, during intervention the region of interest border is present but disappears during angiography exposition conditions.

To conclude the desired effects of the present invention the region of interest overlaying procedure 36 overlays the generated region of interest border geometry on the images acquired through an image acquisition procedure 38.

After the region of interest border overlay is accomplished, the resulting images are output to the display unit 20.

It is to be noted that a re-adjustment of the region of interest border in real time in order to keep the pre-determined accuracy of the object-based registration constant is desirable.

Figure 3:
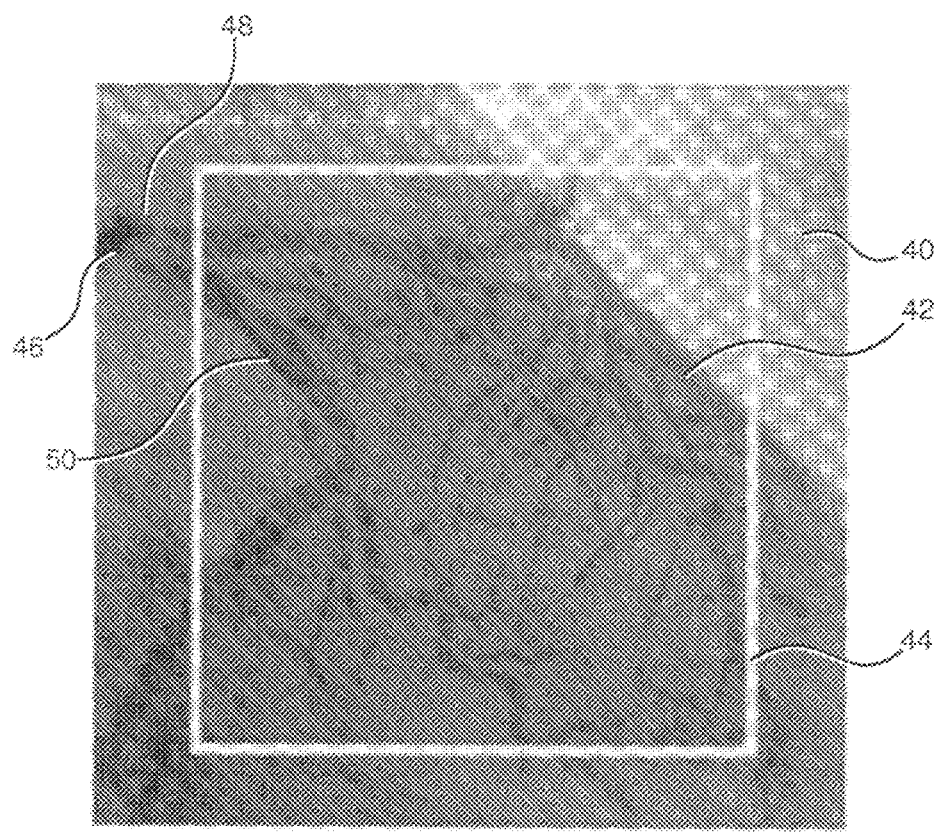
FIG. 3 shows an exemplary region of interest border overlaid on a vessel tree image and a live image.

FIG. 3 schematically shows a fluoroscopic live image 40 of the interventional area. Superposed on this live image 40 are vessel trees 42 that are extracted from an angiogram and are registered by means of an object-based registration technique, which depends on the extent of a considered targeted object visible in the image. For instance during electrophysiology interventions this object can be a pacemaker lead, an electrode, a catheter, etc. This object is used as a reference in order to register the vessel trees and the live images. If the expected object is only partially to be seen, the problem to be solved by the object-based registration algorithm or the like may very well be ill-posed and lead to no solution or to several apparent solutions among which everyone but one are erroneous. This means that different vessel maps, corresponding to different cardiac phases, may completely cover all live images. Anyone of them can be overlaid with the live image, yielding in a possibly erroneous road map. Some of these ambiguities are alleviated by applying temporal constrains on the cardiac cycle continuity. Still, in some cases, the problem is so ill-posed that no satisfactory road mapping can be presented to the clinician.

Figure 4:
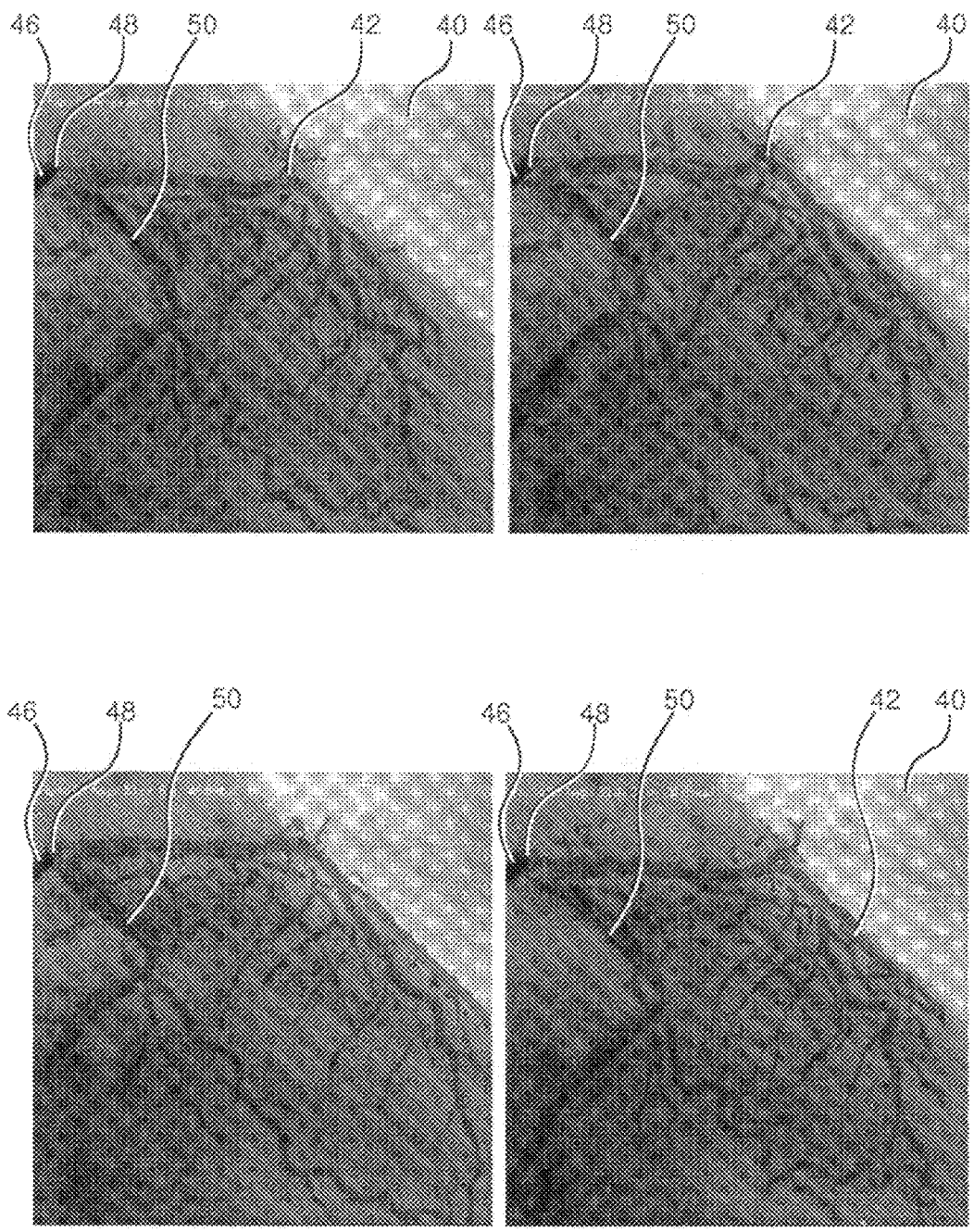
FIG. 4 shows, by way of example, four mathematical solutions to the object-based registration problem posed, in FIG. 3, by the considered targeted object being outside the region of interest border.

By overlaying a region of interest border 44 onto the live image 40 and the vessel trees 42 the medical viewing system according to the present invention may make the clinician aware of the importance of the visibility of the considered target object for the success of the road mapping processing related to the intervention. In the depicted case a catheter 46 is chosen as the considered object and is represented by its tip, which is situated in a vessel 48. The tip of the catheter 46 only extends a very small amount into the live image 40 and it does not reach the region of interest border 44. Since only a very small part of the tip of the catheter 46 is visible it may fit into several or all vessel tree images in the angiogram. Therefore, it is impossible for a road mapping algorithm to identify the right spatial position of the vessel trees when referencing to this hardly visible referenced object yielding in a randomly erroneous solution. FIG. 4 shows four different superposed images of vessel trees on a live image where the tip of the catheter 46 is not moved. All four images are a mathematical solution for the object-based registration problem but obviously the determined position of an exemplarily shown guide wire 48 is not precise as can be seen by a vessel 50 which surrounds the guide wire 48.

Therefore, by means of the displayed border 44 the clinician is made aware that the road mapping procedure might be erroneous if the catheter 46 is not pushed further into the vessel 48 in order to extend over the region of interest border 44. Even though the clinician naturally focuses primarily on the intervention he is carrying on he is lead by the medical viewing system according to the present invention to influence the position of the considered target object in the interventional area in order to allow the object-based registration to work precisely.

While the invention has been illustrated and described in detail in the drawings and forgoing description, such illustration and description are to be considered illustrative or exemplary and not restrictive; the invention is not limited to the disclosed embodiments.

LIST OF REFERENCE SIGNS

10 X-ray imaging system
12 X-ray radiation source
14 table
16 X-ray image detection module
18 data processing unit or calculation unit
20 display unit
22 interface unit
24 generating region of interest border geometry
26 providing geometry parameters
28 providing anatomy priors
30 providing shutter parameters
32 providing system information
34 determination of present exam phase
36 overlaying
38 image acquisition
40 live image
42 vessel tree
44 region of interest border
46 catheter
48 guide wire
50 vessel surrounding guide wire

The invention claimed is:

1. A medical viewing system, the system comprising:
   at least one X-ray image acquisition device for acquiring a pre-interventional angiogram of vessels with injected contrast agent and for acquiring interventional live images thereof;
   at least one display unit; and
   a calculation unit connected to the at least one X-ray image acquisition device and the at least one display unit,
   wherein the calculation unit is configured for registration of vessel tree images extracted from the angiogram relative to the live images through object-based registration and for generating a region of interest border within which at least partial presence of a considered targeted object attains the potential to achieve an accurate registration;
   wherein the display unit is configured for overlaying the region of interest border onto the vessel tree images and the live images.

2. The system according to claim 1, wherein the calculation unit is configured for adjusting at least one of a position, and a size, of the region of interest border according to geometrical parameters of the X-ray image acquisition device, a shutter or both.

3. The system of claim 2, said calculation unit being configured for said adjusting of both said position, and said size, according to said geometrical parameters.

4. The system according to claim 1, wherein the calculation unit is configured for generating a geometry of said region of interest border, said geometry being set to leave a gap corresponding to a range of 10% to 20% of a size of an image acquired via said X-ray image acquisition device.

5. The system according to claim 1, wherein the calculation unit is configured for adjusting the region of interest border to anatomy priors.

6. The system according to claim 1, wherein the calculation unit is configured for determining an exam phase.

7. The system according to claim 1, wherein the calculation unit is configured to, at least one of manually and according to predetermined exam phases, deactivate said overlaying.

8. The system of claim 1, said considered targeted object being elongated, said system being configured such that said accurate registration entails said considered targeted object being disposed so as to extend into said region of interest border.

9. The system of claim 1, said accurate registration corresponding to a predetermined-accuracy threshold.

10. A method for displaying a region of interest on medical images, the method comprising the steps of:
    acquiring a pre-interventional angiogram of vessels with injected contrast agent by means of at least one X-ray image acquisition device;
    acquiring interventional live images thereof;
    registering of vessel tree images extracted from the angiogram relative to the live images through object-based registration by means of a calculation unit connected to the at least one X-ray image acquisition device;
    generating a region of interest border within which at least partial presence of a considered targeted object attains the potential to achieve an accurate registration; and
    overlaying the region of interest border onto the vessel tree images and the live images on at least one display unit connected to the calculation unit.

11. The method according to claim 10, further comprising the step of adjusting at least one of a position, and a size, of the region of interest border according to geometrical parameters of a shutter.

12. The method of claim 11, said step of adjusting comprising adjusting both said position, and said size, according to said geometrical parameters.

13. The method according to claim 10, further comprising the step of generating a geometry of said region of interest border, said geometry being set to leave a gap corresponding to a range of 10% to 20% of a size of an image from among the acquired live images.

14. The method according to claim 10, further comprising the step of adjusting a dimension of the region of interest border to an X-ray image acquisition device angulation angle, to an X-ray image acquisition device rotation angle or to both.

15. The method according to claim 10, further comprising the step of adjusting the region of interest border to anatomy priors.

16. The method according to claim 10, further comprising the step of determining an exam phase.

17. The method according to claim 10, further comprising the step of switching off the overlaying of the region of interest border in predetermined exam phases.

18. The method of claim 10, said considered targeted object being elongated, said region of interest border being configured such that said accurate registration entails said considered targeted object being disposed so as to extend into said region of interest border.

19. A non-transitory computer readable medium embodying a program for displaying a region of interest on medical images, said program having instructions executable by a processor for performing a plurality of acts, among said plurality there being the acts of:

acquiring a pre-interventional angiogram of vessels with injected contrast agent by means of at least one X-ray image acquisition device;

acquiring interventional live images thereof;

registering of vessels extracted from the angiogram relative to the live images through object-based registration by means of a calculation unit connected to the at least one X-ray image acquisition device;

generating a region of interest border within which at least partial presence of a considered targeted object attains the potential to achieve an accurate registration; and overlaying the region of interest border onto the vessel tree images and the live images on at least one display unit connected to the calculation unit.

20. The computer readable medium of claim 19, said considered targeted object being elongated, said accurate registration entailing said considered targeted object being disposed so as to extend into said region of interest border.

* * * * *